United States Patent
Izevbigie

(10) Patent No.: US 6,849,604 B2
(45) Date of Patent: Feb. 1, 2005

(54) PHYTOCHEMOTHERAPY FOR CANCER

(75) Inventor: Ernest B. Izevbigie, Flowood, MS (US)

(73) Assignee: Jackson State University, Jackson, MS (US)

( * ) Notice: Subject to any disclaimer, the term of this patent is extended or adjusted under 35 U.S.C. 154(b) by 0 days.

(21) Appl. No.: 10/756,241

(22) Filed: Jan. 13, 2004

(65) Prior Publication Data

US 2004/0137095 A1 Jul. 15, 2004

Related U.S. Application Data

(62) Division of application No. 10/057,763, filed on Jan. 24, 2002, now Pat. No. 6,713,098.
(60) Provisional application No. 60/264,035, filed on Jan. 24, 2001.

(51) Int. Cl.$^7$ .......................... A61K 38/00; A61K 35/78
(52) U.S. Cl. ............................. 514/15; 514/2; 424/725; 424/774
(58) Field of Search ....................... 514/15, 2; 424/725, 424/774

(56) References Cited

U.S. PATENT DOCUMENTS

| | | |
|---|---|---|
| 5,466,455 A | 11/1995 | Huffstutler, Jr. et al. |
| 6,531,461 B1 | 3/2003 | Nelson |

FOREIGN PATENT DOCUMENTS

| | | |
|---|---|---|
| JP | 6016550 | 1/1994 |
| JP | 6192265 | 7/1994 |

OTHER PUBLICATIONS

Kupchan, S.M., Hemingway, R.J., Kamin, A., and Werner, D. "Tumor inhibitors. XLVII vernodalin and vernomygdin, two new cytotoxin sesquiterpene lactones from *Vernonia amygdalina* Del." *J. Org. Chem.* 34:3908–3911 (1969).

Jisaka, M., Ohigashi, H., takegawa, K., Huffman, M.A., and Koshimizu, K. "Antitumoral and antimicrobial activities of bitter sesquterpene lactones of *Vernonia amygdalina*, a possible medicinal plant used by wild chimpanzees," *Biosci. Biotech. Biochem.* 57:833–834 (1993).

Ojukwu et al., *Bull. Anim. Health Prod. Afr.*, 30(3):257–260. 1982 (VETU abstract).

Almagboul et al., *Fitoterapia*, 59(5):393–396, 1988.

Obatomi et al., *Phytother. Res.*, 11:171–173.

*Primary Examiner*—Christopher R. Tate
(74) *Attorney, Agent, or Firm*—Howrey Simon Arnold & White, LLP

(57) ABSTRACT

The present invention provides for a novel anti-neoplastic pharmaceutical composition. Specifically, the present invention provides for phytochemotherapeutic compositions produced from aqueous extracts (and fractions thereof), derived from *Vernonia amygdalina* leaves. These pharmaceutical compositions inhibit the growth of neoplastic cells, including human breast cancer cells. Furthermore, the instant invention provides for methods of producing the compositions and methods of using the compositions to inhibit the proliferation of neoplastic cells.

17 Claims, 5 Drawing Sheets

PHYTOCHEMOTHERAPY FOR CANCER

This is a divisional of application Ser. No. 10/057,763, filed Jan. 24, 2002; now U.S. Pat. No. 6,713,098 which claims the benefit of U.S. provisional application Ser. No. 60/264,035, filed Jan. 24, 2001.

BACKGROUND OF THE INVENTION

1. Field of the Invention

The present application relates generally to the treatment of neoplastic disease and the compositions employed therein. The instant invention concerns a novel phytochemotherapeutic composition, methods for producing the composition, and use of the composition in a method for treating cancer and other neoplastic diseases. Specifically, the instant invention provides for an aqueous extract, and fractions thereof obtained by chromatographic separation, isolated from *Vernonia amygdalina* (*V. amydalina*) each of which inhibit the growth of cancer cells.

2. Technical Problem Addressed

Breast cancer is the most common form of malignant disease among women in Western countries and, in the United States, is the most common cause of death among women between 40 and 55 years of age (Forrest, 1990). There is a need for improved compositions and protocols for the treatment of human breast cancer and other neoplastic diseases. The instant invention provides phytochemotherapeutic compositions and methods for inhibiting the growth of cancer cells, and specifically for the growth inhibition of human breast cancer cells.

3. Description of Related Art

*Vernonia amygdalina*, a plant known for its very bitter taste, has been shown to sometimes be ingested by chimpanzees suffering from parasite-related diseases (Koshimizu, 1994).

Previous investigation into the possible antineoplastic properties exhibited by *Vernonia amygdalina* have focused on chloroform extractable components. For example (Kupchan et al., 1969) suggests that *Vernonia amygdalina* contains at least three distinct cytotoxic components, namely vernolide, vernodalin, and vernomygdin (see page 3909, Chart I). However, there are no reports of any water-extractable *Vernonia amygdalina* components which exhibit antineoplastic properties.

SUMMARY OF THE INVENTION

The present invention provides for an anti-neoplastic pharmaceutical composition typically comprising filtrates prepared from aqueous extracts of *Vernonia amygdalina* leaves, collected from plants in Benin City, Nigeria. Also provided are pharmaceutical compositions prepared from fractions of the *Vernonia amygdalina* aqueous extracts, prepared by chromatographic separation of the extracts. The instant invention also provides for methods of preparing the *Vernonia amygdalina* aqueous extracts and chromatographic fractions. Additionally the instant invention provides methods for the treatment of neoplastic disease using these *Vernonia amygdalina* extracts and chromatographic fractions. These methods are useful for treating neoplastic disease, especially breast cancer, in animals suffering therefrom.

One embodiment of the instant invention provides for a method of preparing a pharmaceutical composition. In one aspect of this embodiment of the invention the pharmaceutical composition is produced by a process comprising the following steps:

a) Providing *Vernonia amygdalina* leaves.

b) Rinsing the leaves with water.

c) Soaking the leaves in water.

d) Crushing the leaves, preferably in by a gentle means, to produce a mixture.

e) Producing a filtrate by filtering the mixture to remove particulate matter.

f) Optionally, concentrating the filtrate by removing water.

Other embodiments of the instant invention provide for chromatographic separation of the aqueous extract filtrate. This separation may be by any suitable means commonly used, by those of skill in the art, to partition the various components of a complex solution and/or mixture.

Other embodiments of the instant invention provide for anti-neoplastic pharmaceutical compositions prepared from a extract, filtrate, or fraction thereof, isolated by any of the methods described above.

Other embodiments of the invention provide methods of inhibiting the growth and/or proliferation of neoplastic cells, both malignant and non-malignant. According to one aspect of this embodiment of the invention, cancer cell proliferation is inhibited by contacting the neoplastic cells with an effective amount of a pharmaceutical composition produced from an aqueous extraction of *Vernonia amygdalina* leaves. In another aspect of this embodiment of the invention, neoplastic cell proliferation is inhibited by contacting the cells with an effective amount of a pharmaceutical composition produced from a fraction of an aqueous extraction of *Vernonia amygdalina* leaves, wherein the fraction was isolated by chromatographic separation of the aqueous extract.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Following incubation, all cells were pulsed with 1 µCi/ml [$^3$H]thymidine for an additional 4–6 hours as described in Example 2. The results represent the mean±SD of three independent experiments. *P<0.05; **P<0.01.

Figure 4:
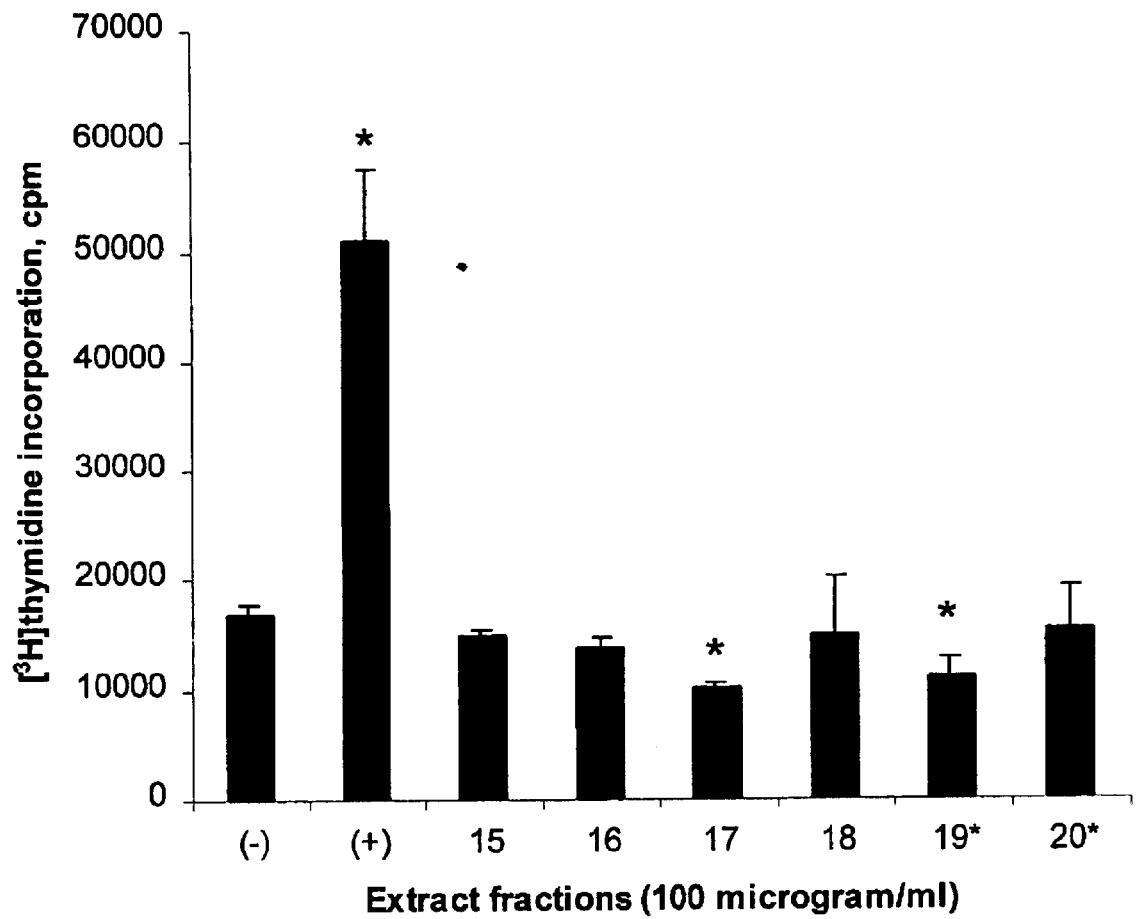

FIG. 4 shows the anti-neoplastic effect of selected and normalized *V. amygdalina* extract fractions sequentially separated by PRPC, prepared as described in Examples 3 and normalized for protein content. Sub-confluent cells were serum-starved overnight and then were left untreated, i.e., no serum (−), were treated with serum (+) or with 100 µg/ml of *V. amygdalina* fractions 15, 16, 17, 18, 19, or 20 for 18 hours. Following incubation, all cells were pulsed with 1 µCi/ml [$^3$H]thymidine for an additional 4–6 hours as described in Example 2. The results represent the mean±SD of three independent experiments. *P<0.05; **P<0.01.

Figure 5:
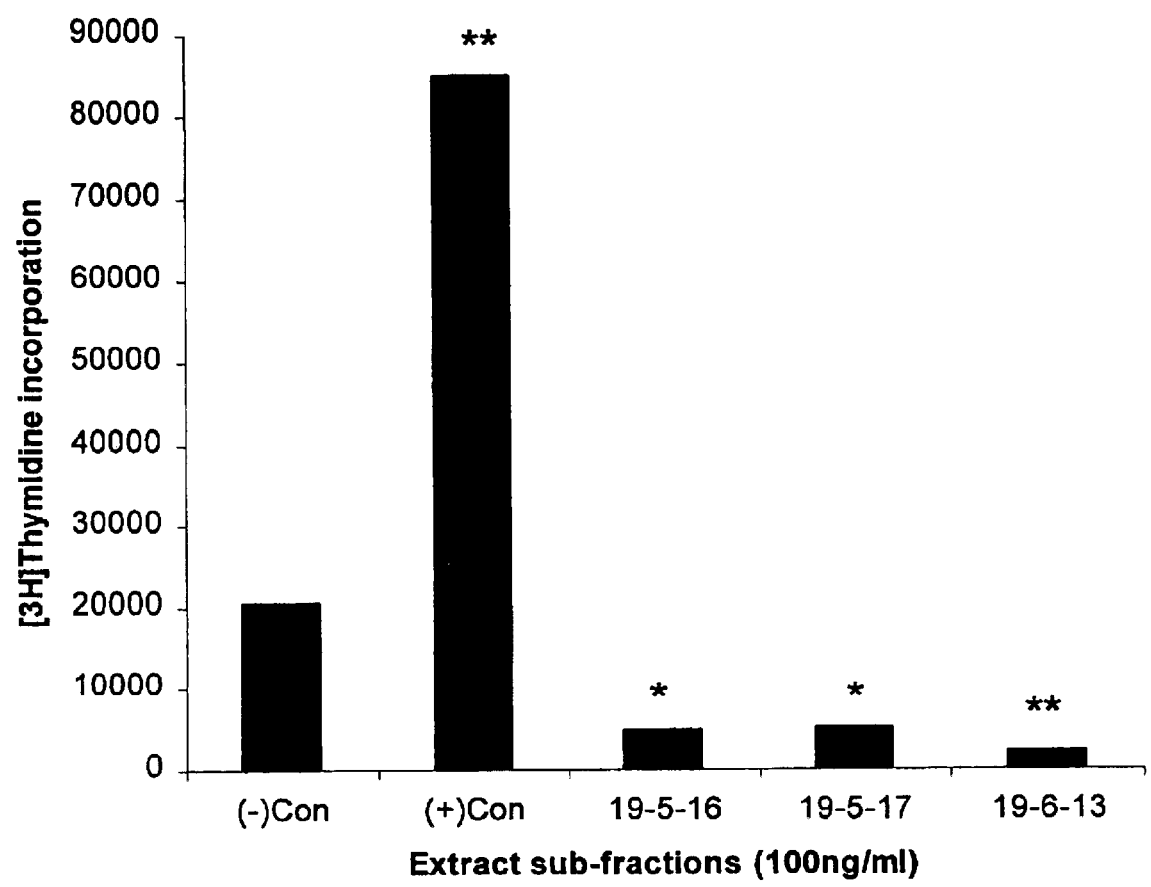

FIG. 5 shows the ant-neoplastic effect of purified *V. amygdalina* extract fractions sequentially separated by preparative reverse phase chromatography, ion exchange chromatography, and reverse phase chromatography (as described in Examples 3–5). Sub-confluent cells were serum-starved overnight and then were left untreated, i.e., no serum (−), were treated with serum (+) or with 100 ng/ml of *V. amygdalina* fractions 19-5-16, 19-5-17, or 19-5-13 for 18 hours. Following incubation, all cells were pulsed with 1 µCi/ml [$^3$H]thymidine for an additional 4–6 hours as described in Example 2. The results represent the mean±SD of three independent experiments. *P<0.05; **P<0.01.

DESCRIPTION OF ILLUSTRATIVE EMBODIMENTS

The present invention provides for pharmaceutical compositions prepared from aqueous extracts of *Vernonia amygdalina*, or fractions thereof. The instant invention also provides for methods of inhibiting neoplastic cell proliferation, particularly breast-cancer cells, using these pharmaceutical compositions. As used herein, the term "neoplastic cells" refers to both cancerous (malignant) and non-malignant cells.

One embodiment of the instant invention provides for an anti-neoplastic pharmaceutical composition. In one aspect of this embodiment of the invention the pharmaceutical composition is produced by a process comprising the following steps:

a) Providing *Vernonia amygdalina* leaves.
b) Rinsing the leaves with water.
c) Soaking the leaves in water.
d) Crushing the leaves, preferably in a gentle manner, to produce a mixture.
e) Producing a filtrate by filtering the mixture to remove particulate matter.
f) Optionally, concentrating the filtrate by removing water.

In this embodiment of the invention it is contemplated that the leaves may be rinsed and soaked in any water of suitable purity. For example, washing may be carried out in distilled or deionized water. Preferably, the water is sterilized (e.g. by either heat or filter sterilization) prior to use.

According to one aspect of the present embodiment the *Vernonia amygdalina* leaves may be crushed by any suitable means. Exemplary methods for crushing the leaves to produce the mixture, which are contemplated for use according to this aspect of the invention, include by are not limited to smashing the leaves using a mortar and pestle and pressing the leaves through a sieve.

In order to separate the particulate matter from the mixture the mixture may be filtered using any means which is compatible with the instant invention. Such means may include but is not limited to filtering through a small mesh sieve, filtering through gauze or a paper filter or filtration through any other commercially available filter.

Following filtration the filtrate may, optionally, be concentrated by any suitable means, including, but not limited to evaporative concentration and lyophilization.

In another aspect of the current embodiment, the process for preparing the pharmaceutical composition may further comprise separating the filtrate (concentrated or not) into multiple fractions using one or more chromatographic methods. Any chromatographic method suitable for the present invention may be used. Exemplary potential chromatographic method(s) include, but are not limited to, partition chromatography (such as hydrophobic interaction chromatography (HIC), ion exchange chromatography (IEC), reverse phase chromatography (RPC), including preparative reverse phase chromatography, and affinity chromatography) and size exclusion chromatography.

In another aspect of this embodiment, the filtrate may be further separated by two or more sequential chromatographic modes. Similarly, in yet another aspect of this embodiment of the invention, the filtrate may be separated into fractions, sub-fractions, and sub-sub-fractions by sequential separation using preparative reverse phase high-performance liquid chromatography (referred to hereinafter as PRPC), IEC, and RPC or any other suitable separation technique. These modes of separation may be performed in any order consistent with the instant invention.

In one particularly preferred aspect of this embodiment of the invention the filtrate is first separated by PRPC to produce PRPC-fractions. The PRPC fractions are then analyzed to determine which fraction(s) has/have the greatest potency against neoplastic cells (as used herein, "potency against neoplastic cells" means having the ability to prevent or reduce the ability of the neoplastic cells to grow, divide (including the ability to replicate its genomic DNA), and/or metastasize). Following the analysis the fraction(s) exhibiting the greatest potency against the neoplastic cells are sub-fractionated by IEC to produce IEC sub-fractions. Next the IEC sub-fractions are analyzed to determine which sub-fraction(s) has/have the greatest potency against neoplastic cells. Once identified, the sub-fraction(s) having the greatest potency against neoplastic cells are further separated by RPC to produce RPC sub-fractions. Finally, as with the IEC sub-fractions, the RPC sub-fractions are analyzed to determine which sub-fractions have the greatest potency against neoplastic cells and these fractions are used to produce an anti-neoplastic pharmaceutical composition. In an even more particular aspect of the invention the composition comprises one or more peptides having the sequence of SEQ ID NO:1 and/or SEQ ID NO:2

According to the instant invention, fractionation of the *Vernonia amydalina* aqueous extract filtrate is typically carried out in order to concentrate and/or further purify the efficacious components of the identified fractions. It is believed that the efficacious components of the current fractions may comprise any water extractable molecule, including but not limited to proteins and/or peptides.

The potency against neoplastic cells, exhibited by the isolated fractions, may be determined by measuring the inhibition of cell growth and/or division of cells treated with the fractions. This analysis may be done using any suitable neoplastic cell line, such cell lines are available from cell culture repositories such as American Type Culture Collection (Manassas, Va.). In one particular aspect of the present embodiment the potency against cancer cells is determined by measuring the pharmaceutical composition's ability to inhibit the growth and/or division of MCF-7 cells (MCF-7 is a human cell line derived from an adenocarcinoma of the breast).

Inhibition of cell growth and/or division may be determined by any suitable means. Exemplary methods for determining inhibition of cell growth and/or division include evaluation of cell membrane using a trypan-blue exclusion assay; determination of DNA replication by measuring the uptake of tritium-labeled thymidine, measurement of cell viability using the methyl thiazolyl tetrazolium (MTT) cell proliferation assay.

Another embodiment of the invention provides for a pharmaceutical composition comprising peptide(s) having the sequence of SEQ ID NO:1 and/or SEQ ID NO:2.

Another embodiment of the instant invention provides for a method of preparing an anti-neoplastic pharmaceutical composition. According to various aspects of this embodiment of the invention, anti-neoplastic pharmaceutical compositions may be prepared by any of the methods, described above. Specifically, the methods may comprise producing a filtrate from an aqueous extract from *Vernonia amygdalina* leaves. According to other aspects of this embodiment of the invention, the method may further comprise subsequent separation and/or concentration of the efficacious components of the filtrate (concentrated or not), accomplished by any suitable chromatographic mode. Chromatographic modes, contemplated as being suitable for this aspect of the invention, include, but are not limited to: partition chromatography (such as hydrophobic interaction chromatography (HIC), ion exchange chromatography (IEC), reverse phase chromatography (RPC), including PRPC, and affinity chromatography) and size exclusion chromatography.

Another aspect of this embodiment of the invention provides for a pharmaceutical composition comprising a purified peptide of SEQ ID NO:1 or SEQ ID NO:2, wherein the peptides are either purified from *V. amygdalina*, or another natural source, or are chemically synthesized.

Another embodiment of the invention provides for a method of inhibiting the proliferation of neoplastic cells and/or the treatment of an animal suffering from neoplastic disease. As used herein the term "neoplastic disease" refers cancer as well as other diseases caused by malignant or benign tumors.

According to this embodiment of the invention, neoplastic cell proliferation is inhibited and/or neoplastic disease is treated by contacting the cells with a pharmaceutical compositions of the present invention, in an amount effective to inhibit and/or reduce cell proliferation. The neoplastic cell inhibition may occur either in vitro or in vivo. Furthermore, the treatment of any susceptible neoplastic cell type is envisioned. One aspect of this embodiment of the invention contemplates treating an animal afflicted with a neoplastic disease, with the pharmaceutical compositions of the instant invention. Particularly, mammals and mammalian cells may be treated using the instantly described pharmaceutical compositions. More particularly, the instant compositions may be used to treat humans. Even more particularly, according to one specific aspect of this embodiment of the invention, human breast cancer cell proliferation may be inhibited by contacting the breast cancer cells with an effective amount of a pharmaceutical composition produced according to the teachings of the instant application. In all embodiments of the instant invention the pharmaceutical compositions is prepared by a process comprising generating a filtrate from an aqueous extraction of *Vernonia amygdalina* leaves.

As used herein an "effective amount" is defined as a dose of the pharmaceutical composition sufficient to measurably reduce cell proliferation. Preferably, an amount sufficient to reduce cell proliferation by more than 10%, 20%, 30%, 40%, 50%, 60%, 70%, 80%, or 90%.

As used herein, the phrase "contacting the cells" includes any suitable means for delivering the pharmaceutical composition to the target cell(s). Contemplated delivery methods include, but are not limited to: direct delivery to the cell growth medium, delivery to an animal via intravenous, or subcutaneous injection, or any other suitable parenteral or non-parenteral delivery method well known to those skilled in the art.

Various additional aspects of this embodiment of the invention are also contemplated. These aspects comprise inhibiting the proliferation of neoplastic cells by contacting the neoplastic cells with a pharmaceutical composition produced by a process which comprises further fractionation of the filtrate by any of the modes described, supra. That is, wherein the filtrate is subjected to further fractionation by one or more chromatographic modes, such as PRPC, HIC, IEC, and/or RPC. In one particular aspect of this embodiment of the invention human breast cancer cells are inhibited by contacting the cells with pharmaceutical composition prepared from constituents isolated by sequential fractionation of the *Vernonia amygdalina* aqueous extract filtrate by PRPC, IEC, and RPC. In one particular aspect of this embodiment of the invention neoplastic cell proliferation is inhibited and/or neoplastic disease is treated by contacting the cells with a pharmaceutical composition comprising a purified protein having the sequence of SEQ ID NO:1 and/or SEQ ID NO:2. The peptides of SEQ ID NO:1 and/or SEQ ID NO:2 may be either purified from *Vernonia amygdalina* or another natural source or may be chemically synthesized.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Crude Extract From *Vernonia Amygdalina*

Example 1

Aqueous Extraction of *Vernonia Amygdalina* Leaves

1. Fresh *Vernonia amygdalina* leaves were collected in Benin City, Nigeria from pesticide-free plants (it is important to note that the plants investigated in the Kupchan et al. report were collected from east Africa, specifically Ethiopia and thus may represent a *Vernonia amygdalina* sub-species with properties distinct from employed for use in the instant invention).
2. 18 grams of *Vernonia amygdalina* leaves were washed three times with distilled water.
3. Next the leaves were soaked overnight (12–18 hours) in 36 mL of distilled water at 4° C.

4. The leaves were then gently smashed (while still in the water), using a mortar and pestle, to prepare a mixture of leaf extract and crushed leaf tissue.
5. The mixture was then filtered through gauze to remove the large particulate matter.
6. An aliquot of the filtered extract was removed and the concentration was determined by measuring its absorption at a wavelength of 600 nm.
7. The filtrate was stored at −20° C.

Example 2

Determination of Cell Growth Inhibition by Measurement of Thymidine Incorporation in Cells Treated with Crude *Vernonia Amygdalina* Leaf Extract 1. MCF-7 cells (a human cell line derived from an adenocarcinoma of the breast, which may be obtained from American Type Culture Collection (ATCC), Manassas, Va.) were passaged followed by propagation, in RPMI 1640 supplemented with 10% Fetal Bovine Serum (FBS) and a 1% pen/strep/fungisone mixture. The RPMI 1640, FBS, and antimicrobial mixture were all purchased from Gibco BRL (Grand Island, N.Y.). The cells were grown in 35 mm tissue culture dishes (Fisher Scientific, Houston, Tex.) in a humidified incubator at 37° C. under an atmosphere of 95% air and 5% $CO_2$, until the cells reached approximately 40% confluence. Fresh medium was supplied every 48 hours. All other chemicals were obtained from Sigma® Chemical Co. (St. Louis, Mo.).
2. The cells were then washed with serum-free medium and serum starved overnight.
3. The various cultures were then treated as described for FIG. 1. (i.e. serum-free medium, medium plus serum, or serum-free medium plus various concentrations of crude water-soluble *Vernonia amygdalina* extract, ranging in concentration from 0.001 to 100 ng/mL) with *Vernonia amygdalina* extract prepared as described in Example 1, and allowed to incubate for 18 hours. Note that prior to adding the extract to the cells, it was filter sterilized by filtering through a 0.45 micron filter.
4. [$^3$H]thymidine (1 mCi/ml, obtained from ICN, Irvine, Calif.) was added to the cell medium to obtain a final concentration of 1 $\mu$Ci/ml and the cells were incubated for an additional 4–6 hours.
5. The medium was aspirated from the cell monolayers and the cells were washed three times with ice-cold PBS, pH 7.5 (purchased from Gibco BRL).
6. 2 mL of 10% trichloroacetic acid (TCA) was added to each 35 mm tissue culture dish followed by incubation at 4° C. for 15 minutes.
7. The cells were then washed three times with ice-cold water.
8. 1 mL of 0.5 M NaOH was added to each 35 mm tissue culture dish and the cells were then incubated at 37° C. for 30 minutes.
9. Next, the contents of the dish were transferred to a 5 mL scintillation vial containing 4 mL of scintillation cocktail (Packard Instruments Corp., Meriden, Conn.) and the radioactivity present was determined by measurement in a scintillation counter.

Figure 1:
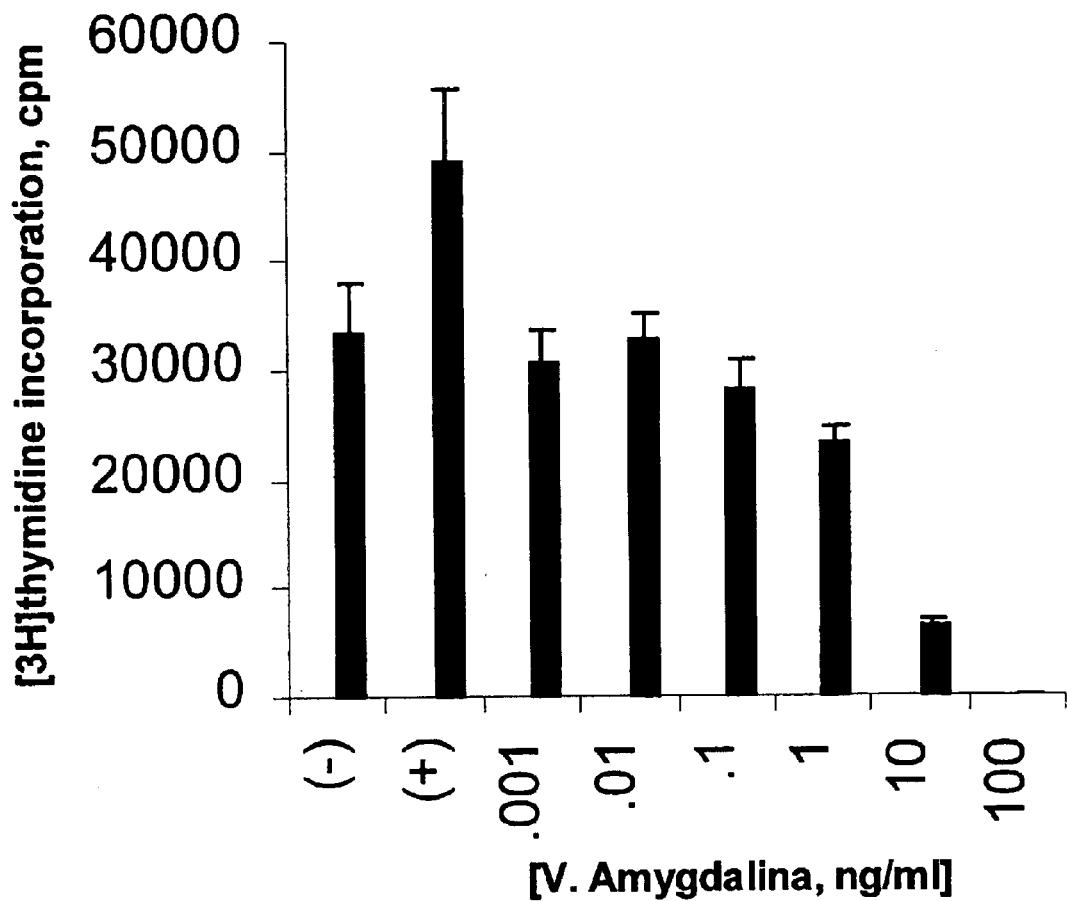
FIG. 1 shows the effect on cell proliferation when human breast cancer cells are contacted with a water-soluble extract of *Vernonia amygdalina*. The experiments summarized in FIG. 1. were performed as follows: sub-confluent cells were serum-starved overnight. Following serum starvation the cells were treated with various concentrations of water-soluble *Vernonia amygdalina* extract (in the range from 0.001–100 ng/mL). Note that the concentration refers to the mass of solute per milliliter of solution. Negative control (−) cultures were left untreated, that is, cultured in medium lacking fetal bovine serum. Positive control (+) cultures received medium supplemented with 10% fetal bovine serum. Each result represents the mean (±SD) for three independent experiments.
Figure 2:
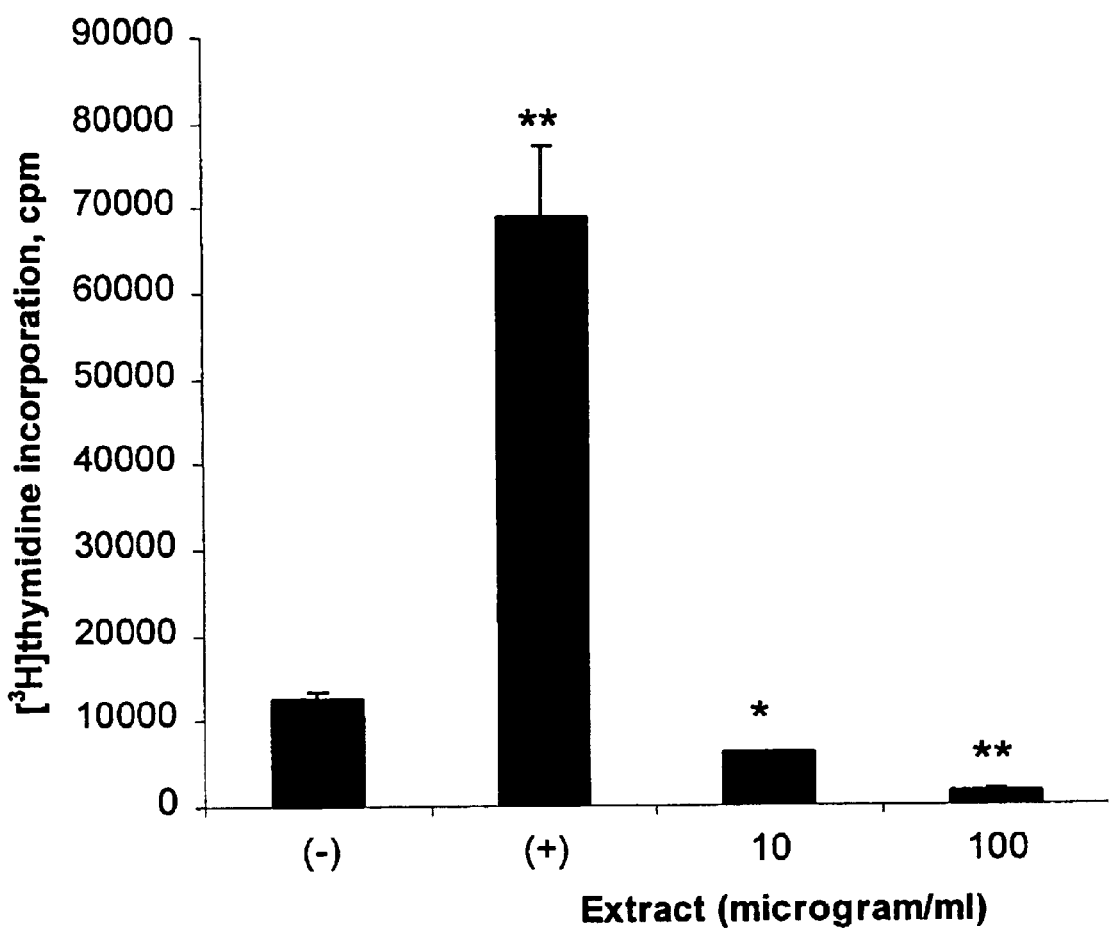
FIG. 2 shows the anti-neoplastic effect of water soluble extract, from an independent extraction of *V. amygdalina* leaves, on human breast cancer cells (MCF-7). The cells were treated as described in FIG. 1.
Figure 3:
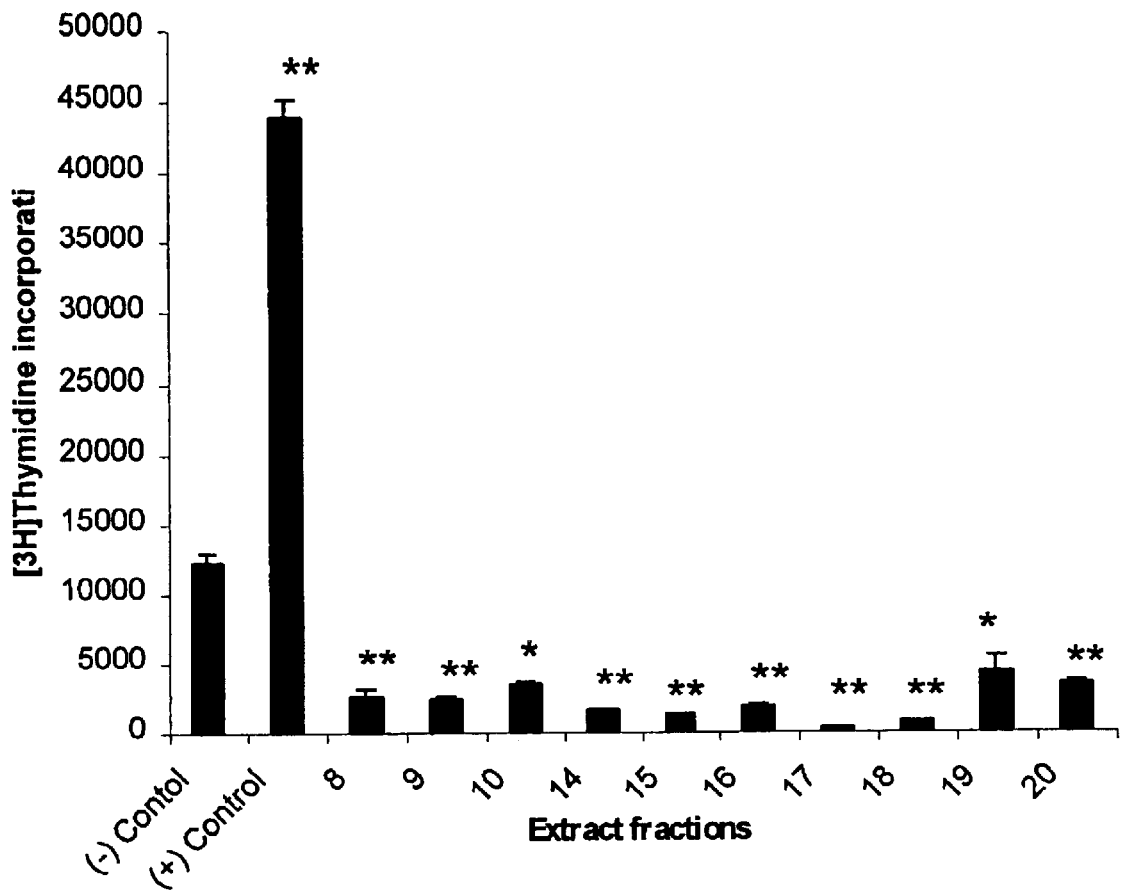
FIG. 3 shows the anti-neoplastic effect of various *V. amygdalina* extract fractions separated by preparative reverse phase high-performance liquid chromatography (referred to hereinafter as PRPC), prepared as described in Example 3. Sub-confluent cells were serum-starved overnight and then were left untreated, i.e., no serum (−), were treated with serum (+) or with isolated *V. amygdalina* fractions 8, 9, 10, 14, 15, 16, 17, 18, 19, or 20 for 18 hours.

The results of this experiment are summarized in FIG. 1. Significantly, the instant pharmaceutical composition exhibits an $ED_{50}$ (the dosage necessary to inhibit cell growth by 50%) value of 0.005 $\mu$g/mL. This is more than 300-fold more efficacious than vernomygdin, as reported Kupchan et al. (1969) for the inhibition of nasopharynx carcinoma cells (see Table 1.), and more than 22-fold more effective than vernodalin, as reported by Jisaka et al. (1993) for the inhibition of mouse leukemia cells (see table on page 834). Results of a similar experiment conducted on a *Vernonia amygdalina* leaves independently harvested and extracted are shown in FIG. 2.

Fractionated and Standardized *Vernonia Amygdalina* Extracts

Example 3

Preparative Reverse Phase High-Performance Liquid Chromatography of Crude *Vernonia Amygdalina* Extract 1. The water-soluble fraction of *V. amydalina* (prepared as described in example 1) was lyophilized and then dissolved in 10 ml TRIS-HCl buffer, pH 7.0 (this is a buffer prepared by dissolving the TRIS (Tris[hydroxymethyl] aminomethane) in water and adjusting the pH with hydrochloric acid).
2. 900 ml of ethanol was added and the proteins were precipitated by incubating the solution at −20° C. for 24 hours.
3. The protein pellets were collected by centrifugation at 2500 rpm in a Sorvall® SS-34 rotor in a Sorvall® RC-5B centrifuge (at −20° C. for 35 minutes).
4. The pellets were then washed twice with a methanol:chloroform (9:1) mixture.
5. The pellets were then dissolved in 1 ml of 4 M guanidine HCl.
6. Samples of the protein solution were loaded on a $C_{18}$ column (25 mm×250 mm, 300 Å, 5 $\mu$m, purchased from Vydac Company, Herperia, Calif.) and separated by preparative reverse phase high-performance liquid chromatography (hereinafter referred to as PRP).
7. The fractions were eluted with a linear gradient of buffer A (0.1% trifluoroacetic acid, water) and buffer B (0.1% trifluoroacetic acid in acetonitrile). The gradient progressed from 5% buffer B to 70% buffer B in 60 minutes (at 10 mL/min.). The mixture was then held at 70% buffer B for an additional 6 minutes. A total of twenty-two fractions were collected between 0 and 66 minutes, with samples taken at 3 minute intervals (see Table 1)*

*Ten of the 22 preparative reverse phase HPLC fractions were biologically active these were fractions 8, 9, 10, and 14–20.

TABLE 1

Preparative Reverse Phase HPLC fractions

| Time (in minutes) | Fraction Number |
|---|---|
| 0–3 | 1 |
| 3–6 | 2 |
| 6–9 | 3 |
| 9–12 | 4 |
| 12–15 | 5 |
| 15–18 | 6 |
| 18–21 | 7 |
| 21–24 | 8 |
| 24–27 | 9 |
| 27–30 | 10 |
| 30–33 | 11 |
| 33–36 | 12 |
| 36–39 | 13 |
| 39–42 | 14 |
| 42–45 | 15 |
| 45–48 | 16 |
| 48–51 | 17 |

TABLE 1-continued

Preparative Reverse Phase HPLC fractions

| Time (in minutes) | Fraction Number |
|---|---|
| 51–54 | 18 |
| 54–57 | 19 |
| 57–60 | 20 |
| 60–63 | 21 |
| 63–66 | 22 |

Example 4

Ion Exchange Chromatography (IEC) of PRPC Fractions

1. Selected samples, specifically fractions 17 and 19 were diluted each to 125 ml with 20 mM Tris-buffer, pH 8.5 and loaded separately on a 25 mm×150 mm TSK-DEAE (Diethylaminoethyl) column.
2. The column was then washed with 250 ml of starting buffer, i.e. 20 mM Tris, pH 8.5.
3. The column was next developed with a eluting buffer having a linear concentration gradient beginning with 20 mM Tris and ending with 20 mM Tris+800 mM KCl, pH 8.5 over 55 minutes. Fractions were collected in 5 minute intervals. This resulted in 10 sub-fractions each for PRPC fractions 17 and 19, for a total of 20 sub-fractions.

Example 5

Reverse Phase Chromatography (RPC) of IEC Sub-Fractions

1. Each of the 20 sub-fractions obtained in Example 4 were individually loaded on a 10 mm×250 mm $C_{18}$ (Vydac Company, Herperia, Calif.).
2. The columns were washed with 25 ml of 0.1% trifluoroacetic acid:5% acetonitrile:water.
1. The columns were then developed with a eluting solution with a linear concentration gradient beginning with 0.1% trifluoroacetic acid:5% acetonitrile:water and ending with 0.1% trifluoroacetic acid:80% acetonitrile:water
2. For each of the 20 IEC sub-fractions, 35 RPC sub-fractions were obtained. The resulting 700 RPC fractions (20×35) were lyophilized.

Example 6

Determination of Cell Growth Inhibition of MCF-7 Cells by Measurement of Thymidine Incorporation in Cells Treated with PRPC Fractions of *Vernonia Amygdalina* Extract A cell growth inhibition assay was performed as described in Example 2, with the exception noted below.

The treated cells were incubated for 24 hours with PRPC fractions of the crude *Vernonia amygdalina* extract. Due to the limited size of the fractions only 10 µg/ml was used for samples treated with fractions 19 and 20, whereas 100 µg/ml were used for the samples treated with the remaining fractions. The results demonstrated that, when adjusted for equal protein concentrations the order of potency was as follows (most potent to least potent): fraction 19>20>17>16>18>15 (there was no detectable activity in the other fractions).

Example 7

Determination of Cell Growth Inhibition of MCF-7 Cells by Measurement of Thymidine Incorporation in Cells Treated with of Crude *Vernonia Amygdalina* Extract Sequentially Fractionated by PRPC, IEC, and RPC Fraction 19 of the PRPC separation described in Example 3 was subjected to IEC fractionation as described in Example 4 to produce 10 IEC sub-fractions designated IEC sub-fractions 19-1 to 19-10. Subsequently, sub-fraction 19-5 was further fractionated by RPC to produce 35 RPC sub-fractions, designated RPC sub-fractions 19-5-1 through 19-5-35. Three of the RPC sub-fractions of 19-5, namely, 19-5-13, 19-5-15, and 19-5-16 exhibited exceptionally high potency in a growth inhibition assay conducted as described in Example 6. These sub-fractions inhibited cell DNA synthesis by 10-fold, 4-fold, and 4-fold, respectively at a concentration of 100 nanograms/ml (See FIG. 5). Finally, Two RPC sub-fractions, specifically 19-5-16 and 19-5-17, were further analyzed and shown to be pure peptides. The sequences of these peptides are, for 19-5-16: Asp Thr Lys Asp Val Val Asn Val Thr Gly (SEQ ID NO:1); and for 19-5-17: Xaa Xaa Val Leu Ala Gly Ala Asp Gln Met Xaa Ile Ile Gly Glu (SEQ ID NO:2). For SEQ ID NO:2 the identity of the amino acids at positions 1 and 2 is uncertain and the identity of the amino acid at position 11 is thought to be serine, but this is not entirely certain.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention as defined by the appended claims.

References

The following references, to the extent that they provide exemplary procedural or other details supplementary to those set forth herein, are specifically incorporated herein by reference.

Forrest, A. P. "Screening and breast cancer incidence." *J. Natl. Cancer Inst.*, 82:1525, 1990.

Koshimizu, K., Ohigashi, H., and Huffman, M. A. "Use of *Vernonia amygdalina* by wild chimpanzee: possible roles of its bitter and related constituents." *Physiol. Behav.* 56:1209–1216,1994.

Kupchan, S. M., Hemingway, R. J., Kamin, A., and Werner, D. "Tumor inhibitors. XLVII vernodalin and vernomygdin, two new cytotoxin sesquiterpene lactones from *Vernonia amygdalina* Del." *J. Org. Chem.* 34:3908–3911 (1969).

Jisaka, M., Ohigashi, H., Takegawa, K., Huffman, M. A., and Koshimizu, K. "Antitumoral and antimicrobial activities of bitter sesquterpene lactones of *Vernonia amygdalina*, a possible medicinal plant used by wild chimpanzees," *Biosci. Biotech. Biochem.* 57:833–834 (1993).

What is claimed is:

1. A pharmaceutical composition comprising one or more purified polypeptide(s), the polypeptide(s) comprising the sequence(s) of SEQ ID NO:1 and/or SEQ ID NO:2.

2. The pharmaceutical composition of claim 1 wherein the polypeptide is isolated from a natural source or chemically synthesized.

3. The pharmaceutical composition of claim 2 wherein the polypeptide is purified from *Vernonia amygdalina* leaves.

4. The pharmaceutical composition of claim 2 wherein the polypeptide is chemically synthesized.

5. The pharmaceutical composition of claim 1 wherein the polypeptide(s) consists of the sequence of SEQ ID NO:1 and/or SEQ ID NO:2.

6. The pharmaceutical composition of claim 1 comprising a purified polypeptide comprising the sequence of SEQ ID NO:1.

7. The pharmaceutical composition of claim 1 comprising a purified polypeptide comprising the sequence of SEQ ID NO:2.

8. A method of treating an animal afflicted with a neoplastic disease comprising administering to the animal an effective amount of a pharmaceutical composition comprising one or more purified polypeptide(s), the polypeptide(s) comprising the sequence(s) of SEQ ID NO:1 and/or SEQ ID NO:2.

9. The method of claim 8 where the polypeptide is isolated from a natural source or chemically synthesized.

10. The method of claim 9 wherein the polypeptide is purified from *Vernonia amygdalina* leaves.

11. The method of claim 9 wherein the polypeptide is chemically synthesized.

12. The method of claim 8 wherein the purified polypeptide comprises the sequence of SEQ ID NO:1.

13. The method of claim 8 wherein the purified polypeptide comprises the sequence of SEQ ID NO:2.

14. The method of claim 8 wherein the animal is human.

15. The method of claim 8 wherein the neoplastic disease is breast cancer.

16. The method of claim 8 wherein the purified polypeptide consists of the sequence of SEQ ID NO:1.

17. The method of claim 8 wherein the purified polypeptide consists of the sequence of SEQ ID NO:2.

* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Vernonia amygdalina

<400> SEQUENCE: 1

Asp Thr Lys Asp Val Val Asn Val Thr Gly
1               5                   10

<210> SEQ ID NO 2
<211> LENGTH: 15
<212> TYPE: PRT
<213> ORGANISM: Vernonia amygdalina
<220> FEATURE:
<221> NAME/KEY: MISC_FEATURE
<222> LOCATION: (1)..(2)
<223> OTHER INFORMATION: Xaa = Any
<220> FEATURE:
<221> NAME/KEY: MISC_FEATURE
<222> LOCATION: (11)..(11)
<223> OTHER INFORMATION: Xaa = Ser or Any

<400> SEQUENCE: 2

Xaa Xaa Val Leu Ala Gly Ala Asp Gln Met Xaa Ile Ile Gly Glu
1               5                   10                  15
```